United States Patent [19]

Okawa et al.

[11] Patent Number: 5,969,187
[45] Date of Patent: Oct. 19, 1999

[54] PROCESS FOR PRODUCING TRANS 1,4-BIS(AMINOMETHYL)CYCLOHEXANE

[75] Inventors: Takashi Okawa; Tomoo Tsujimoto; Hideo Ikarashi; Masaharu Doya; Yutaka Kanbara, all of Niigata, Japan

[73] Assignee: Mitsubishi Gas Chemical Company, Inc., Japan

[21] Appl. No.: 09/030,794

[22] Filed: Feb. 26, 1998

[30] Foreign Application Priority Data

Mar. 17, 1997 [JP] Japan ................................. 9-63145
May 8, 1997 [JP] Japan ................................ 9-118162

[51] Int. Cl.$^6$ ................................................ C07C 209/88
[52] U.S. Cl. ................................................................ 564/444
[58] Field of Search ........................................... 564/444

[56] References Cited

U.S. PATENT DOCUMENTS 3,767,707 10/1973 Cleary .
4,058,563 11/1977 Richter .

FOREIGN PATENT DOCUMENTS 28 11 722   9/1978   Germany .
46-16979    5/1971   Japan .
46-30835    9/1971   Japan .
1351553     5/1974   United Kingdom .
1554698    10/1979   United Kingdom .

OTHER PUBLICATIONS

I. Hashimoto et al., *Yuuki Gosei Kagaku*, 25(2), 46–49 (1967).

*Primary Examiner*—Brian M. Burn
*Attorney, Agent, or Firm*—Wenderoth, Lind & Ponack, L.L.P.

[57] ABSTRACT

Provided a process for producing higher content of trans 1,4-bis(aminomethyl)cyclohexane which is used as the raw material for producing polyamides or polyurethanes having physically and chemically excellent properties from 1,4-bis(aminomethyl)cyclohexane which is generally produced by hydrogenation of p-xylylenediamine.

That is, a mixture of cis and trans 1,4-bis(aminomethyl)cyclohexane is isomerized by heating at 120 to 250° C. in the presence of a platinum group catalyst to change to trans isomer. 1,4-bis(aminomethyl)cyclohexane containing more than 80% trans isomer is produced by combining this isomerization technique and crystallization technique.

5 Claims, No Drawings

PROCESS FOR PRODUCING TRANS 1,4-BIS(AMINOMETHYL)CYCLOHEXANE

BACKGROUND OF THE INVENTION

1) Field of the Invention

The present invention relates to a process for producing the trans-isomer of 1,4-bis(aminomethyl)cyclohexane and more particularly concerned with a process for producing a higher content of trans 1,4-bis(aminomethyl)cyclohexane from a mixture of the cis isomer and trans isomer.

2) Description of the Prior Art 1,4-bis(aminomethyl)cyclohexane is an industrially important compound as a raw material for polyamides. Diisocyanate obtained from the 1,4-bis(aminomethyl)cyclohexane is useful as a raw material for polyurethanes.

1,4-bis(aminomethyl)cyclohexane has two stereoisomers of trans isomer and cis isomer and the content of trans-isomer influences the physical properties of the polyamides and polyurethanes.

For instance, in the case of polyamides produced from 1,4-bis(aminomethyl) cyclohexane and suberic acid, the higher content of trans-isomer improves melting point and heat stability. So more favorable polymers for fibers, films and plastic elements are obtained by using a higher content of trans-isomer. In the case of polyurethanes produced from polyalcohols and diisocyanate derived from 1,4-bis(aminomethyl)cyclohexane, higher content of trans isomer improves solubility in solvents.

So, it is expected to develop a process for producing more valuable 1,4-bis(aminomethyl)cyclohexane which contains more trans 1,4-bis(aminomethyl) cyclohexane.

1,4-bis(aminomethyl)cyclohexane is produced generally by hydrogenation of p-xylylenediamine. The selective production of trans isomer in this process is difficult because more cis isomer is produced than trans isomer. The content of trans isomer in this process is less than 40%, so the isomerization method or separation method to obtain the product may be considered to produce a higher content of trans-isomer of 1,4-bis(aminomethyl)cyclohexthane.

Concerning isomerization of the alicyclic amines, isomerization of bis(4-aminocyclohexyl)methane which has three stereoisomers of trans-trans type, cistrans type and cis-cis type is known. Methods of increasing the content of bis(4-aminocyclohexyl)methane of trans-trans type by isomerization by heating higher than 130° C. using a catalyst of ruthenium oxide, nickel or cobalt and hydrogen are disclosed in Japanese Patent Publication No. 46-16979 and Japanese Patent Publication No. 46-30835. In U.S. Pat. No. 4058568, there is described a method for producing a higher content of trans-trans bis(4-aminocyclohexyl) methane by synthesizing an imine compound from bis(4-aminocyclohexyl)methane and benzaldehyde, isomerizing the imine compound with alkali catalyst and hydrolyzing the isomerized imine compound with acid.

As the separation method for producing higher content of trans 1,4-bis(aminomethyl)cyclohexthane, the distillation method or crystallization method may be considered. However, in general, the distillation method requires a multi-stage distillation column to separate cis isomer and trans isomer because the boiling points of these isomers are very close.

Although the separation method of crystallization and the content of trans isomer are not disclosed, it is described in the Japanese magazine Yuuki Gosei Kagaku (Organic Chemistry) vol. 25, No. 2 page 46 (1967) that the amount of white crystals obtained is increased by keeping 1,4-bis(aminomethyl)cyclohexane at 0 to −5° C. and the peak of the trans isomer obtained by gas chromatography of these white crystals become large.

However, when this method is used with 1,4-bis(aminomethyl)cyclohexthane which is produced by hydrogenation of p-xylylene diamine and the content of trans isomer is less than 40%, the yield of trans isomer is very low because mutual solubilities of two isomer are large. Even if the recovery from the mother liquor is repeated, more than 60% of 1,4-bis(aminomethyl)cyclohexane remains as cis isomer theoretically.

The first object of the present invention is to increase the content of trans isomer of 1,4-bis(aminomethyl) cyclohexthane which is generally produced by hydrogenation of p-xylylene diamine and is used as a raw material for polyamide and polyurethane products that have excellent physical or chemical properties.

The second object of the present invention is to provide a method to obtain 1,4-bis(aminomethyl)cyclohexane containing more than 80% of trans isomer with high yield from bis(aminomethyl)cyclohexane containing the cis and trans isomers.

SUMMARY OF THE INVENTION

As a result of an extensive study for an isomerization of cis 1,4-bis(aminomethyl)cyclohexthane to trans isomer, the present inventors have found that cis isomer is changed to trans isomer by heating in the presence of a platinum group catalyst.

That is, the first invention provides the method for isomerization, which comprises heating cis 1,4-bis(aminomethyl)cyclohexane at 120 to 250° C. in the presence of a platinum group catalyst and changing it to trans isomer.

By raising the temperature of isomerization in this method, the content of trans isomer is increased and about 80% trans 1,4-bis(aminomethyl)cyclohexane is obtained. However, the yield of 1,4-bis(aminomethyl)cyclohexane is decreased at such a high temperature because side reactions are increased.

As a result of more study of the method for producing trans 1,4-bis(aminomethyl)cyclohexane, the present inventors have found that 1,4-bis(aminomethyl)cyclohexane containing more than 80% of trans isomer is obtained with high yield by combining isomerization of cis to trans isomer and separation of trans isomer and cis isomer by crystallization where the content of trans isomer is increased within allowable loss by side reactions in isomerization, and the mother liquor from crystallization is recycled to the isomerization in this process.

That is, the second invention provides the process for producing trans 1,4-bis(aminomethyl)cyclohexane which comprises isomerizing from cis to trans isomer by heating raw 1,4-bis(aminomethyl)cyclohexane 120 to 250° C. in the presence of a platinum group catalyst in the first step by the first invention, separating the crystals of high content trans 1,4-bis(aminomethyl)cyclohexane from the isomerized liquid by crystallization at second step, and recycling the mother liquor separated from crystallization to the first process to isomerize.

DETAILED DESCRIPTION OF THE INVENTION

The 1,4-bis(aminomethyl)cyclohexane used as a raw material in the present invention is useful for polyamides and polyurethanes. This 1,4-bis(aminomethyl) cyclohexane is generally produced by hydrogenation of p-xylylenediamine using ruthenium or rhodium catalyst. The content of trans 1,4-bis(aminomethyl) cyclohexane trans type is generally 20–40%, so much cis isomer of bis(aminomethyl)cyclohexane is contained.

Platinum group catalyst which is used for isomerization at the first invention contains the metals or compounds of ruthenium, rhodium, palladium, osmium, iridium and platinum. For instance, the catalysts supported ruthenium, rhodium, palladium, osmium, iridium, platinum only or mixtures of them on carbon, alumina, silica, diatomaceous earth, etc. are used. For the examples of compounds, oxides, inorganic or organic salts and organo-metallic compounds like acetylacetonate are used for the catalyst. A supported catalyst which is easy to separate from the products is preferably used, and especially supported catalysts of ruthenium or rhodium are preferable. The amount of the catalyst used as weight ratio of platinum group metal to 1,4-bis (aminomethyl)cyclohexane is more than 0.001 weight percent, generally in the range of 0.01 to 10 weight percent.

Solvent is not necessarily required, however, solvent is preferably used because side reaction is suppressed and the reactions are performed uniformly using the solvent. An inert solvent to the reaction is used for the solvent. For instance, ammonia; amines such as butylamine, aniline, hexylamine, etc.; aliphatic or aromatic hydrocarbons such as hexane, cyclohexane, benzene, toluene, mesitylene, etc; aliphatic alcohols such as methanol, ethanol, cyclohexanol, etc.; aliphatic ethers such as propylether, tetrahydrofuran, dioxane, etc. are used for the solvent. Particularly, ammonia is preferable because side reactions like dimerization are suppressed by using ammonia. The amount of solvent used in weight ratio to 1,4-bis(aminomethyl)cyclohexane is 0.1 to 10.

This isomerization reaction may use inert gas such as nitrogen, argon or helium. However, reactive gas like hydrogen decreases the yield of 1,4-bis(aminomethyl) cyclohexane. So the isomerization of the present invention is preferably carried out without using hydrogen.

The temperature of the isomerization is 120 to 250° C. and preferably 150 to 200° C. The content of trans 1,4-bis (aminomethyl)cyclohexane is increased at higher temperature. However, side reactions are increased when the reaction temperature is higher than 250° C. When the reaction temperature is lower than 120° C., isomerization of cis to trans isomer is decreased.

The reaction time depends upon the amount of the catalyst, the reaction conditions and the method of the reaction. Usually, the reaction time is in the range of several minutes to 3 hours.

This isomerization is carried out batchwise or flowwise. In the batchwise reaction, for instance, raw materials of 1,4-bis(aminomethyl)cyclohexane, solvent, a supported catalyst of platinum group and inert gas if required are charged to a tank type reactor together, then isomerization is carried out by heating with stirring. Catalyst is separated from reacted products by using a filter. Solvent and 1,4-bis (aminomethyl)cyclohexane are separated by the distillation of the mother liquor. In the flowwise reaction, for instance, a tube reactor filled with a supported platinum group catalyst is heated, then 1,4-bis(aminomethyl)cyclohexane raw material and solvent are charged to carry out isomization. Solvent and 1,4-bis(aminomethyl)cyclohexane are separated by distillation of products.

The second embodiment of the present invention comprises the first step of isomerization of cis 1,4-bis (aminomethyl)cyclohexane to trans isomer and the second step of separation of trans 1,4-bis(aminomethyl) cyclohexane by crystallization.

The crystals of trans 1,4-bis(aminomethyl)cyclohexane which contains more than 80% of the trans isomer are separated by crystallization and recycled to the second step.

Solvent is not necessarily required in the second step. However, solvent is preferably used because viscosity of 1,4-bis(aminomethyl)cyclohexane is increased at low temperatures and the handling of filtration becomes difficult. A solvent which is inert to 1,4-bis(aminomethyl)cyclohexane and a melting point of lower than −9° C. may be used in the second step. A solvent of lower solubility to trans crystals is preferred. Branched or cyclic hydrocarbon compounds like hexane, methylcyclohexane, toluene and xylene are used preferably, and n-hexane is especially preferred.

Crystallization is carried out by mixing 1,4-bis (aminomethyl)cyclohexane and solvent, then cooling at −9 to 27° C. Slurry containing crystals is separated to crystals and mother liquor by using a filter or centrifugal separator. The crystals obtained mainly containing trans isomer product are heated to liquefy them, and then 1,4-bis (aminomethyl)cyclohexane containing a higher content of the trans isomer is separated from solvent by distillation. The mother liquor is recycled to the first step for isomerization together with raw material.

The first step and the second step in the second embodiment are carried out batchwise, flowwise or by a method which is combined batchwise and flowwise. A continuous process in which isomerization of the first step and crystallization of the second step are operated continuously comprises, for instance, isomerizer, ammonia recovery column, crystallizer, filter and solvent recovery columns. Platinum group supported catalysts are filled to the isomizer. 1,4-bis(aminomethyl)cyclohexane which is obtained by hydrogenation of p-xylylenediamine, for instance, is fed with liquid ammonia solvent to the top of isomerizer. From the reacted solution, ammonia is recovered at the ammonia recovery column.

The isomerized solution from the first step is mixed with solvent and cooled in a crystallizer in the second step. Then crystals of 1,4-bis(aminomethyl) cyclohexane containing much trans isomer are separated from solvent by distillation. The mother liquor is recycled to the first step to isomerize with raw material.

According to the present invention, as shown in following example, cis 1,4-bis(aminomethyl)cyclohexane is isomerized to more valuable trans isomer.

That is, according to the first invention, the content of trans isomer is easily increased from 1,4-bis(aminomethyl) cyclohexane containing less trans isomer which is produced by hydrogenation of p-xylylenediamine.

And according to the second embodiment, 1,4-bis (aminomethyl)cyclohexane containing more than 80% of the trans isomer is produced in high yield by combining the technique of isomerization from cis isomer to trans isomer and crystallization to separate trans isomer and cis isomer.

From this 1,4-bis(aminomethyl)cyclohexane containing much trans isomer, products of polyamide and polyurethane having excellent physical and chemical proporties are obtained. So the industrial significance of the present invention is great.

PREFERRED EMBODIMENT OF THE INVENTION

The present invention will be described in detail below, referring Examples which are not limitative to the present invention.

EXAMPLE 1

Isomerization by the First Invention

In a 100 ml shaking type stainless autoclave, 4 g of 1,4-bis(aminomethyl) cyclohexane (referred to as 1,4-BAC), 2 g of 5% ruthenium catalyst supported on granular carbon (referred to as 5%-Ru/C catalyst) were charged and closed. The ratio of trans isomer to cis isomer of the 1,4-BAC was 28.4%/71.6%. 16 g of liquid ammonia was charged to the autoclave with nitrogen gas to achieve a total pressure 50 kg/cm$^2$. This autoclave was equipped with a shaker in an electric heater, and was heated to 200° C. for one hour to react. Then the autoclave was cooled and purged of residual gases. The reaction product was separated from the catalyst by a filter and analyzed by gas chromatography. As the result, a ratio of trans isomer to cis isomer of the 1,4-BAC became 76.3%/23.5%/23.5%.

EXAMPLE 2

The isomerization was carried out in the same manner as in Example 1 except that a catalyst supported 5% ruthenium on aluminum powder was used. As a result, the ratio of trans isomer to cis isomer of the 1,4-BAC became 68.6%/31.4%.

EXAMPLE 3

The isomerization was carried out in the same manner as in Example 1 except that the reaction temperature was set to 175° C. As a result, the ratio of trans isomer to cis isomer of the 1,4-BAC became 62.5%/37.5%.

EXAMPLE 4

4 g of 1,4-BAC, 16 g of mesitylene and 2 g of 5%-Ru/C catalyst were charged to the same autoclave as Example 1. Then the autoclave was pressurized to 50 kg/cm$^2$ with nitrogen gas and isomized for 30 minutes at 175° C. As the result, the ratio of trans isomer to cis isomer of the 1,4-BAC became 63.7%/36.3%.

EXAMPLE 5

The isomerization was carried out in the same manner as in Example 3 except that a catalyst supported 5% ruthenium on aluminum powder was used. As a result, the ratio of trans isomer to cis isomer of the 1,4-BAC became 60.1%/39.9%.

EXAMPLE 6

The isomerization was carried out in the same manner as in Example 3 except that the autoclave was pressurized to 100 kg/cm$^2$ with hydrogen gas instead of nitrogen gas. As a result, the ratio of trans isomer to cis isomer of the 1,4-BAC became 61.2%/38.8%.

Comparative Example 1

The isomerization was carried out in the same manner as in Example 1 except that the reaction temperature was set to 100° C. As a result, the ratio of trans isomer to cis isomer of the 1,4-BAC was 27.8%/72.2%.

Comparative Example 2

The isomerization was carried out in the same manner as in Example 1 except that 2 g of 58% nickel catalyst supported on diatomaceous earth instead of 5% Ru/C catalyst was used. As a result, the ratio of trans isomer to cis isomer of the 1.4-BAC was 29.6%/70.4%.

Referential Example

Hydrogenation of p-xylylenediamine

The flowwise reaction of hydrogenation of p-xylylenediamine was carried out using a stainless tube reactor of 30 mm diameter and 1 m length. 252 g (=415 ml) of 2% ruthenium catalyst supported on alumina was charged to the reactor tube. The height of the catalyst bed was 60 cm. Hydrogen gas was charged from the upper part of the reactor and purged at 60 liters/hour, keeping a pressure of 100 kg/cm$^2$. Heating the reactor to 125° C., aqueous solution containing 20% of p-xylylenediamine was charged to the upper side of the reactor at 430 g/h. In a stationary state, reacted solution was sampled to analyze with a gas chromatography. As the result, the yield of 1,4-BAC to raw material p-xylylenediamine was 83.7%. Water was distilled off using a rotary-evaporator from the reacted solution. Then residual solution was distilled using 14 stage packed tower and 1,4-BAC of more than 99.9% purity was obtained by the distillation. The ratio of trans isomer to cis isomer of the 1,4-BAC obtained was 34.0%/66.0%.

EXAMPLE 7

The First Step of the Second Embodiment

In a 500 ml stirring type stainless steel autoclave, 40 g of 1,4-BAC obtained in REFERENTIAL EXAMPLE, 5 g of 5%-Ru/C catalyst were charged and closed. The ratio of trans type to cis isomer of the 1,4-BAC was 34.0% to 66.0%. 160 g of liquid ammonia was charged to the autoclave with nitrogen gas to achieve total pressure 50 kg/cm$^2$. This autoclave was equipped with an electric heater, and was heated to 175° C. for one hour. Then the autoclave was cooled and the residual gas was purged. The reaction product was separated into catalyst and mother liquid by a filter. Then the mother liquid was simply distilled to exclude ammonia and 1,4-BAC was separated by vacuum distillation. The 1,4-BAC was analyzed by gas chromatography. As a result, the ratio of trans isomer to cis isomer of the 1,4-BAC became 62.5%/37.5% and the recovery ratio of 1,4-BAC was 88.4%.

EXAMPLE 8

The Second Step of the Second Embodiment)

10 g of isomerized solution obtained in EXAMPLE 7 and log of n-hexane were charged to a 50 ml flask. After the inner gas was exchanged with nitrogen, the flask was closed and stirred thoroughly. This flask was kept in a refrigerator at −1° C. for a night and a day to crystallize 1,4-BAC trans isomer. The contents were separated into crystals and mother liquor by a filter and the crystals are dried by vacuum.

The recovery ratio of crystals to the isomerized solution was 15.2%. And the content of trans isomer in the crystals determined by analyzing aqueous solution of the crystals with gas chromatography was more than 99.9%. The ratio of trans isomer to cis isomer in the mother liquor was 58.3%/41.6%.

EXAMPLE 9

When Mother Liquor from the Second Step was Recycled 2 g of 1,4-BAC (trans isomer to cis isomer was 34.0/66.0%) and 2 g of mother liquor obtained from EXAMPLE 8 (trans isomer to cis isomer was 58.1/41.6%) and 2 g of 5%

Ru/C catalyst were charged to a 100 ml stainless shaking type autoclave and closed. Then 16 g of liquid ammonia and nitrogen gas was charged to the autoclave and kept at a total pressure of 50 kg/cm². This autoclave was equipped in a shaker with an electric heater, and was heated to 175° C. for one hour to react. Then the autoclave was cooled and residual gas was purged. The reaction product was separated to catalyst and mother liquid by a filter. Then the mother liquid was analyzed with gas chromatography. As a result, the ratio of trans isomer to cis isomer of the 1,4-BAC was 63.1%/36.9% and the recovery ratio of 1,4-BAC was 90.8%.

EXAMPLE 10

When Solvent was not Used in the Second Step 10 g of isomerized solution obtained in EXAMPLE 7 (the ratio of trans isomer to cis isomer was 62.5/37.5%) was charged to a 50 ml flask. After the inner gas was exchanged with nitrogen, the flask was closed and stirred thoroughly. This flask was kept in a refrigerator at 0° C. for a night and day to crystallize 1,4-BAC trans isomer. The contents were separated into crystals and mother liquor by a filter and the crystals were dried by vacuum.

The recovery ratio of crystals to the isomerized solution was 9.5%. The aqueous solution of the crystals was analyzed by gas chromatography. The ratio of trans isomer to cis isomer of the crystals was 86.8/13.2% and that of the mother liquor was 60.5/39.5%.

EXAMPLE 11

When Mother Liquor and Catalyst from Second Step were Recycled 4 g of 1,4-BAC obtained in REFERENTIAL EXAMPLE (the ratio of trans isomer to cis isomer was 34.0/66.0%) and 2 g of mother liquid obtained from EXAMPLE 10 (the ratio of trans isomer to cis isomer was 60.5/39.5%) and 2 g of 5%Ru/C catalyst recovered from reaction product in EXAMPLE 3 were charged to the autoclave used and closed. Then 16 g of liquid ammonia and nitrogen gas were charged to the autoclave and kept at a total pressure of 50 kg/cm². This autoclave was equipped in a shaker with an electric heater, and was heated to 175° C. for one hour to react. Then the autoclave was cooled and purged of residual gas. The reaction product was separated into catalyst and mother liquor by a filter. Then the mother liquor was analyzed by gas chromatography. As a result, the ratio of trans isomer to cis isomer of the isomerized solution was 60.2%/39.8% and the recovery ratio of 1,4-BAC was 89.6%.

COMPARATIVE EXAMPLE 3

When High Temperature was Used in the First Step 2 g of 1,4-BAC obtained in REFERENTIAL EXAMPLE (trans isomer to cis isomer was 34.0/66.0%) and 2 g of 5%Ru/C catalyst were charged to the autoclave used in EXAMPLE 9 and closed. Then 16 g of liquid ammonia and nitrogen gas were charged to the autoclave and it was kept at total pressure of 50 kg/cm². This autoclave was equipped in a shaker with an electric heater, and was heated to 175° C. for one hour. The reaction product was separated into catalyst and mother liquor by a filter. Then the mother liquor was analyzed by gas chromatography. As a result, the ratio of trans isomer to cis isomer of the isomerized solution was 77.4%/22.6% and the recovery ratio of 1,4-BAC was 62.1%.

What is claimed is:

1. A method for isomerization of 1,4-bis(aminomethyl) cyclohexane which consists essentially of heating cis 1,4-bis(aminomethyl)cyclohexane at 120 to 250° C. in the presence of a platinum group catalyst to isomerize it in the absence of hydrogen and optionally in the presence of ammonia to trans isomer.

2. The method for isomerization of 1,4-bis(aminomethyl) cyclohexane according to claim 1 wherein the platinum group catalyst comprises ruthenium and/or rhodium.

3. The method for isomerization of 1,4-bis(aminomethyl) cyclohexane according to claim 1 wherein the isomerization is carried out in the presence of ammonia.

4. A process for producing trans 1,4-bis(aminomethyl) cyclohexane, which comprises isomerizing cis 1,4-bis (aminomethyl)cyclohexane at 120 to 250° C. in the presence of a platinum group catalyst to form an isomerized liquor containing trans isomer in a first step, separating crystals of the trans isomer from the isomerized liquor by crystallization in a second step, and recycling the mother liquor separated by crystallization to the first step to isomerize it.

5. The process for producing trans 1,4-bis(aminomethyl) cyclohexane according to claim 4, wherein the trans isomer is separated by crystallization using n-hexane.

* * * * *